United States Patent [19]

Botsco et al.

[11] Patent Number: 4,840,066

[45] Date of Patent: Jun. 20, 1989

[54] ULTRASONIC THICKNESS GAUGE HAVING AUTOMATIC TRANSDUCER RECOGNITION AND PARAMETER OPTIMIZATION AND METHOD THEREOF

[75] Inventors: Ronald J. Botsco, Huntington Beach; Robert L. Jones, Anaheim; David E. Methe, Lake Forest, all of Calif.

[73] Assignee: NDT Instruments, Inc., Huntington Beach, Calif.

[21] Appl. No.: 211,791

[22] Filed: Jun. 27, 1988

[51] Int. Cl.⁴ .............................................. G01N 29/00
[52] U.S. Cl. .......................................... 73/597; 73/620
[58] Field of Search ................. 73/597, 620, 627, 633; 324/72.5

[56] References Cited

U.S. PATENT DOCUMENTS

| | | | |
|---|---|---|---|
| 3,720,199 | 3/1973 | Rishton et al. | 128/1 D |
| 4,097,837 | 6/1978 | Cyr | 340/5 C |
| 4,102,205 | 7/1978 | Pies et al. | 73/626 |
| 4,244,227 | 1/1981 | Rudolph et al. | 73/633 |
| 4,391,124 | 7/1983 | Drost et al. | 73/1 DV |
| 4,407,298 | 10/1983 | Lentz et al. | 128/713 |
| 4,437,332 | 3/1984 | Pittaro | 73/627 |
| 4,446,715 | 5/1984 | Bailey | 73/1 R |
| 4,462,082 | 7/1984 | Thiele et al. | 364/571 |
| 4,611,304 | 9/1986 | Butenko et al. | 364/571 |
| 4,648,078 | 3/1987 | Darton et al. | 367/13 |
| 4,672,306 | 6/1987 | Thong | 324/72.5 |
| 4,695,955 | 9/1987 | Faisandier | 364/413 |
| 4,700,708 | 10/1987 | New, Jr. et al. | 128/633 |
| 4,748,598 | 5/1988 | Kopke | 367/13 |
| 4,768,496 | 9/1988 | Kreizman et al. | 123/24 A |

Primary Examiner—Stewart J. Levy
Assistant Examiner—Louis M. Arana
Attorney, Agent, or Firm—Leonard Tachner

[57] ABSTRACT

A measurement system employs a method and apparatus for uniquely tagging each of a plurality of transducers, automatically recognizing the tag for identifying the transducer and automatically adjusting electronic parameters of the system for enhancing performance with a selected transducer. In a preferred embodiment, a resistor is inserted in a piezoelectric transducer of an ultrasonic thickness gauge, a current source and A to D converter measure the resistor and a microprocessor-based logic system adjusts measurement parameters of the gauge to be automatically optimized for the associated transducer characteristics.

3 Claims, 7 Drawing Sheets

ULTRASONIC THICKNESS GAUGE HAVING AUTOMATIC TRANSDUCER RECOGNITION AND PARAMETER OPTIMIZATION AND METHOD THEREOF

BACKGROUND OF THE INVENTION

1. Field of the Invention

The present invention relates generally to ultrasonic thickness gauges and more specifically to an ultrasonic thickness gauge having an automatic transducer recognition feature which permits the gauge to automatically and properly adjust various pertinent electronic parameters within the gauge to achieve optimum performance for the particular transducer recognized.

2. Prior Art

One of the major disadvantages of prior art ultrasonic thickness gauges has been the need for the operator to properly select controls and control parameters for the particular transducer selected for a given gauging application. The numerous types of ultrasonic thickness gauging applications which exist require a variety of different transducer designs in order to provide satisfactory performance of the gauge. In an attempt to maintain relatively simplistic operation of ultrasonic thickness gauges for typically non-technical operator, manufacturers of prior art ultrasonic thickness gauges have generally compromised gauge performance and versatility by offering only a few different transducers with their gauges. Some gauge designs offer the ability to manually adjust internal electronic controls to permit the gauge to function with a "non-standard" transducer. However, this internal adjustment must usually be performed by a technical specialist, thus creating a major inconvenience. Furthermore, after such adjustment, the gauge will no longer operate at peak performance with the standard probes or transducers unless again readjusted by the technical specialist.

One attempt to overcome this problem to a minor degree that is practiced by several manufacturers of ultrasonic thickness gauges, involves provision for automatically adjusting only the thickness range and decimal point position setting of the gauges by means of a multiple-pin-keyed connector on the gauge end of the transducer cable. However, this is a less than satisfactory solution because a special transducer cable connector is required and because it is still possible to connect the wrong transducer to the other end of the cable thereby detrimentally affecting the performance of the gauge. Equally important, this scheme is not practical to address a host of other settings and adjustments actually necessary to enhance performance.

There has therefore been a long felt need for an ultrasonic thickness gauge which is provided for use with a wide variety of different transducers and which can automatically adjust gauge performance parameters to optimally accommodate the particular transducer selected without requiring that the operator have any special skill or knowledge to make such adjustments manually.

SUMMARY OF THE INVENTION

The present invention solves the aforementioned long felt need by providing a gauge which automatically recognizes each of a wide variety of transducers and then automatically and properly adjusts critical electronic parameters within the gauge to achieve optimum performance for the transducer and the application selected. The resultant gauge and transducer combination provides improved performance, greater reliability and simpler operation with far more versatility. The invention comprises two principal portions. A first such portion in one particular embodiment consists of up to thirty-two (32) different transducers, each with a resistor of predetermined value implanted in the transducer in parallel with the piezoelectric element. Although the present invention utilizes resistors for this purpose, it will be understood that other electrical components can be used to tag each transducer so that it can be automatically recognized by special circuits within the gauge. The resistor values are selected so that they do not affect the normal ultrasonic performance of the transducer. More specifically, there are no shunting effects. Because an ultrasonic piezoelectric transducer has low frequency electrical parameters resembling a capacitor with a very large resistive component in parallel, the value and electrical positioning of the tagging resistor in the transducer can be selected so that it has no effect on the performance on the transducer while it still is readily discernable and easily differentiated from resistors of other values which tag different transducers.

The second portion of the present invention comprises the transducer recognition circuits within the thickness gauge. In the particular embodiment disclosed herein, such recognition circuits are provided in the form of a microprocessor-based digital implementation for both the transducer recognition function and the associated gauging and control circuits. The microprocessor is designed to intermittently sample its input port to determine what value of parallel resistor is present in the transducer, thereby identifying the required gauging parameters from a preassigned lookup table in a memory. During its transducer recognition operation, the circuit first disables the pulser portion of the gauge and then energizes a switch which disconnects a probe damping resistor and connects a precision current source and an A to D converter to the transducer. This is done in order to prevent ambiguities in the code resistor measurement process which would otherwise result from a repetitious pulser signal being transmitted during the resistor code measurement. After the precision current source and A to D converter are connected to the transducer by the microprocessor, analog-to-digital conversion is commanded. The results are read and the microprocessor then checks the lookup table and automatically sets optimum system parameters as defined by the transducer in accordance with the sensed resistor tag within the transducer.

There are numerous thickness gauging circuit parameters that can be automatically controlled by the microprocessor in response to the measured tagging resistor value. By way of example, various parameters in the pulser circuit, receiver circuit, logic circuit and display circuits can be modified to optimize the performance of the gauge in association with identified transducer. Although a particular embodiment of the invention is disclosed herein for use with thickness gauges, the inventive concept disclosed herein can be readily applied to other ultrasonic instruments which use a transducer or a variety of transducers such as industrial flaw detectors, bond testers, bolt gauges, medical ultrasound equipment, and process control monitors including airborne ultrasonic types. Furthermore, the basic invention can be extended to include other types of nondestructive testing instruments which employ a wide variety of probes such as eddy current and microwave testers. The present invention facilitates the use of conventional, standard transducer coax cables including conventional, standard coax cable connectors thereby overcoming a significant disadvantage of the prior art.

OBJECTS OF THE INVENTION

It is therefore a principal object of the present invention to provide a method and apparatus for measuring thicknesses using an ultrasonic thickness gauge which can automatically identify the transducer selected for the particular task and establish optimum gauge parameters for use in conjunction with the selected transducer.

It is an additional object of the present invention to provide an improved ultrasonic thickness gauge/transducer combination in which a wide variety of selectable transducers are each tagged with a discernable and distinct electrical component recognizable by the gauge for permitting an automatic selection by the gauge electronics of optimum measurement parameters for the tagged transducer sensed by the gauge.

It is still an additional object of the present invention to provide an improved ultrasonic thickness gauge in which optimum parameters of the gauge are established for a selected transducer automatically within the electronics of the gauge without requiring the operator to provide any form of manual adjustments.

It is still an additional object of the present invention to provide an improved ultrasonic thickness gauge in which there is automatic parameter adjustment within the gauge electronics for optimum operation with a selected transducer and without requiring the use of non-standard or non-conventional coaxial cables connecting the transducer to the gauge.

BRIEF DESCRIPTION OF THE DRAWINGS

The aforementioned objects and advantages of the present invention as well as additional objects and advantages thereof will be more fully understood hereinafter as a result of a detailed description of a preferred embodiment when taken in conjunction with the following drawings in which.

DETAILED DESCRIPTION OF A PREFERRED EMBODIMENT

Figure 1:
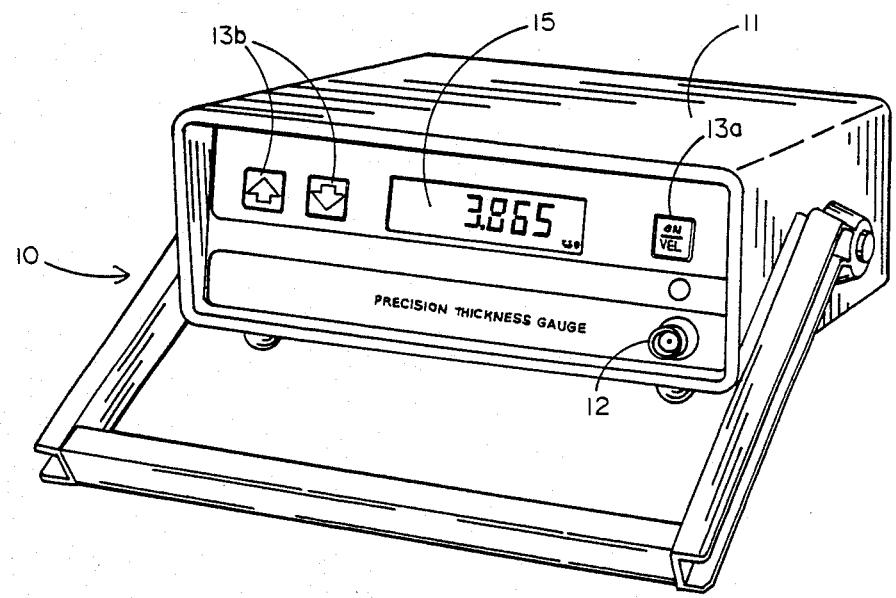
FIG. 1 is an isometric view of the precision thickness gauge of the present invention.

Referring first to FIG. 1 it will be seen that the improved gauge 10 of the present invention comprises a housing 11 having a transducer port 12 and a minimum number of control buttons 13 including an on/off and velocity selection switch 13a and a pair of velocity selection scroll controls 13b. There is also provided a digital display 15. Those having skill in the art to which the present invention pertains will recognize that there is a paucity of controls on the gauge 10 as compared to conventional precision thickness gauges. This highly advantageous reduction in the number of parametric controls that must ordinarily be made available to the user in order to optimize gauge performance is made possible in the present invention by a unique auto-recognition feature which automatically recognizes the selected transducer and then properly sets the pulser characteristics transducer damping the auto zero value receiver characteristics and a host of logic and gating functions as well as the thickness readout range and gauging precision. Even the velocity controls 13b may be ignored in those situations where calibration may be performed on a material of known thickness. Alternatively, velocity controls 13b may be used to select a known velocity of a given material whose thickness cannot be initially calibrated.

Figure 2:
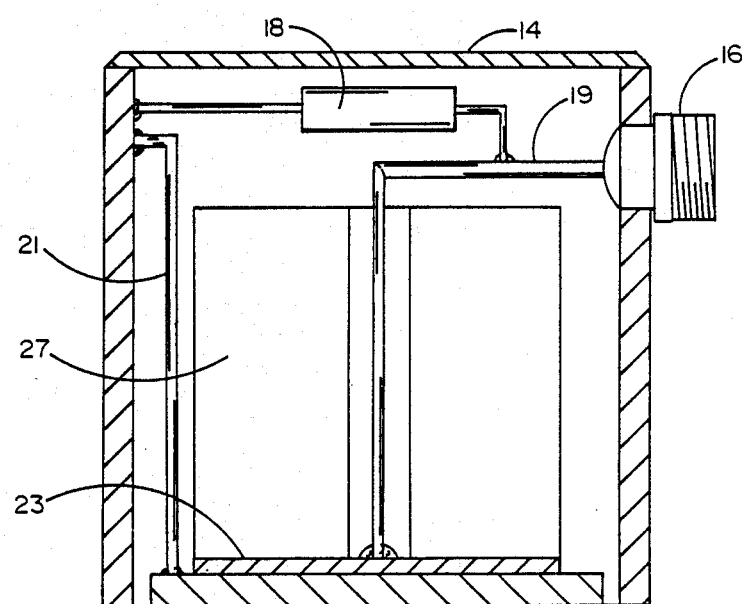
FIG. 2 is a cross-sectional view of the transducer of the present invention.

The transducer of the present invention is shown in cross-section in FIG. 2. More specifically, transducer 14 comprises conventional components such as a connector 16 adapted to connect to a coax cable which is connected at the other to transducer port 12 seen in FIG. 1. Also included in transducer 14 are conventional elements including a positive lead 19, a negative lead 21, a piezoelectric element 23, a wear surface 25 and mechanical backing 27. However unlike conventional transducers used in the thickness gauging art, the unique transducers 14 of the present invention also provides a code or tagged resistor 18 the resistance of which is selected to correspond to a particular transducer so that measurement of the resistance by the gauge 10 will automatically identify the transducer.

Figure 3:
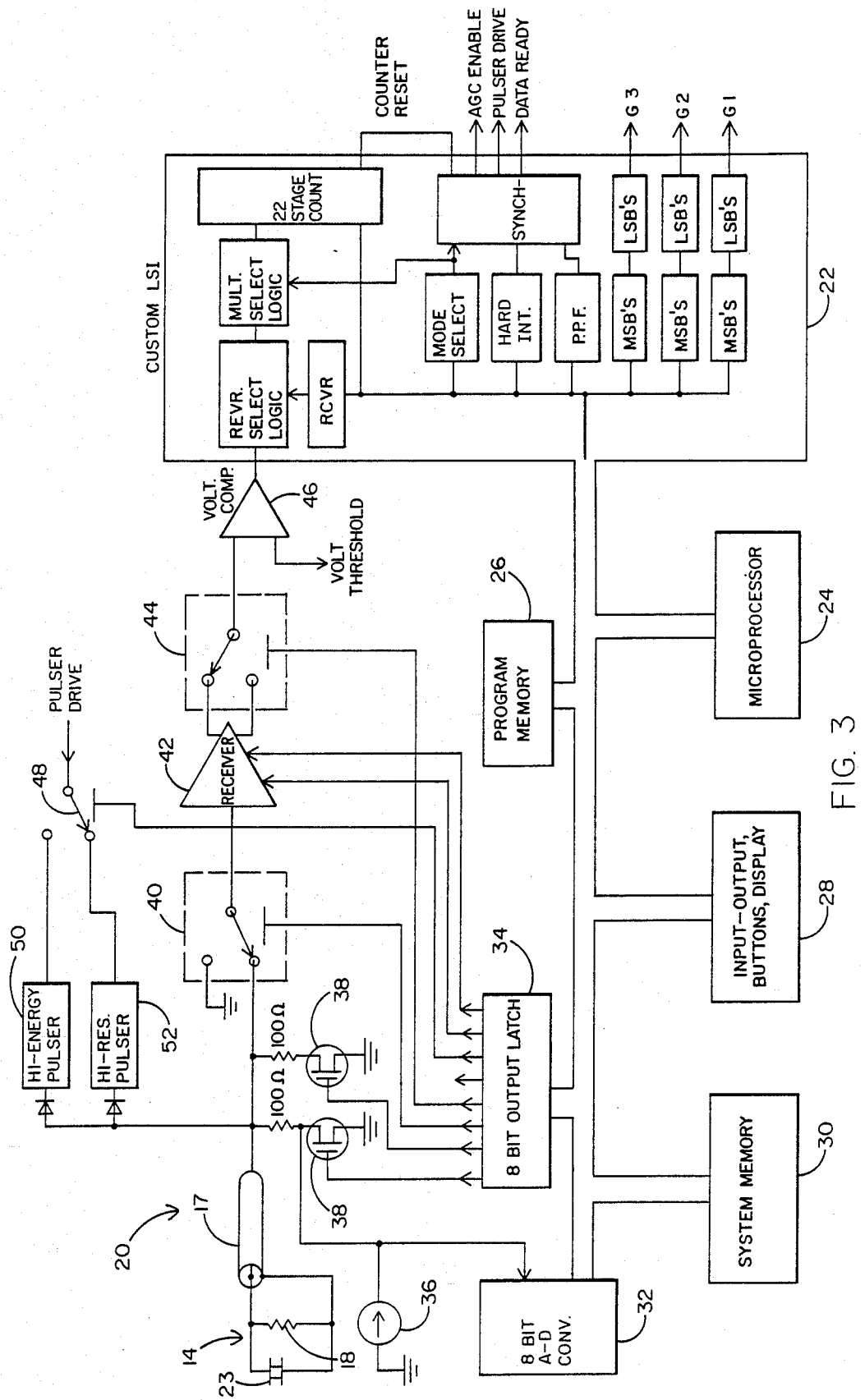
FIG. 3 is a block diagram/schematic drawing of the present invention.

The manner in which the resistor 18 within transducer 14 is recognized by the gauge 10 is shown schematically in FIG. 3 which illustrates the gauge circuit 20. As shown in FIG. 3, gauge circuit 20 comprises gauge control logic 22, microprocessor 24, program memory 26, system memory 30, A to D converter 32, output latch 34 and current source 36. It will be understood that the present invention relates to the transducer recognition and automatic parameter adjustment function described herein and not to the more conventional aspects of thickness measurement. Accordingly, the disclosure herein will relate principally to the novel features of the thickness gauge of the present invention and not to the more conventional features which are well known in the art. By way of example, U.S. Pat. No. 4,715,008 issued Dec. 22, 1987 Jones and assigned to the assignee of the present invention, thoroughly discloses the implementation and operation of those gauging aspects of the present invention which do not relate to the automatic recognition and adjustment features hereof. Accordingly, the aforementioned issued patent is hereby incorporated herein by reference and none of the features described therein will be described in this application.

Thus for example, while the gauge control logic 22 and microprocessor 24 provide significant functions relevant to the present invention, they also provide more conventional functions for actually making and processing the thickness measurement after the transducer has been recognized and the gauging parameters have been set. However, only the recognition and adjustment features and the attendant elements making the recognition and adjustment features possible will be described herein.

Again referring to FIG. 3 it will be seen that the gauge circuit 20 also comprises a pair of transistor switches 38 as well as switches 40 and 44 and 48, a receiver 42, a voltage comparator 46, a pulser drive switch 48 and pulsers 50 and 52. Furthermore, it will be seen that the transducer 14 of the present invention, is connected to the gauge circuit 20 by means of a coaxial cable 17.

Because the gauging circuit 20 of the present invention must perform two distinct functions, namely, its usual thickness measurement function as well as the transducer recognition and parameter setting function, it is effectively provided with the capability for switching between two modes. Thus for example, because receiver 42 is a high gain receiver, during the measurement of the value of the resistor 18 within the transducer 14, switch 40 grounds the input to the receiver 42 so that the receiver is effectively isolated from the measurement of the resistor 18. In addition, there are two one-hundred Ohm damping resistors that form part of the gauging circuit 20 devoted to the pulse echo measurement process. These one-hundred Ohm damping resistors provide a load on the transducer during the actual thickness measurement to damp out disturbances when the pulser 50 or 52 fires the transducer 14. These damping resistors are switched out of the circuit during measurement of resistor 18 by transistor switches 38 controlled by eight bit output latch 34 which is in turn controlled by microprocessor 24. One of the damping resistors remains in series with the transducer during the recognition measurement to preclude damage in the event a non-tagged transducer is inadvertently connected to the gauge.

Figure 4:
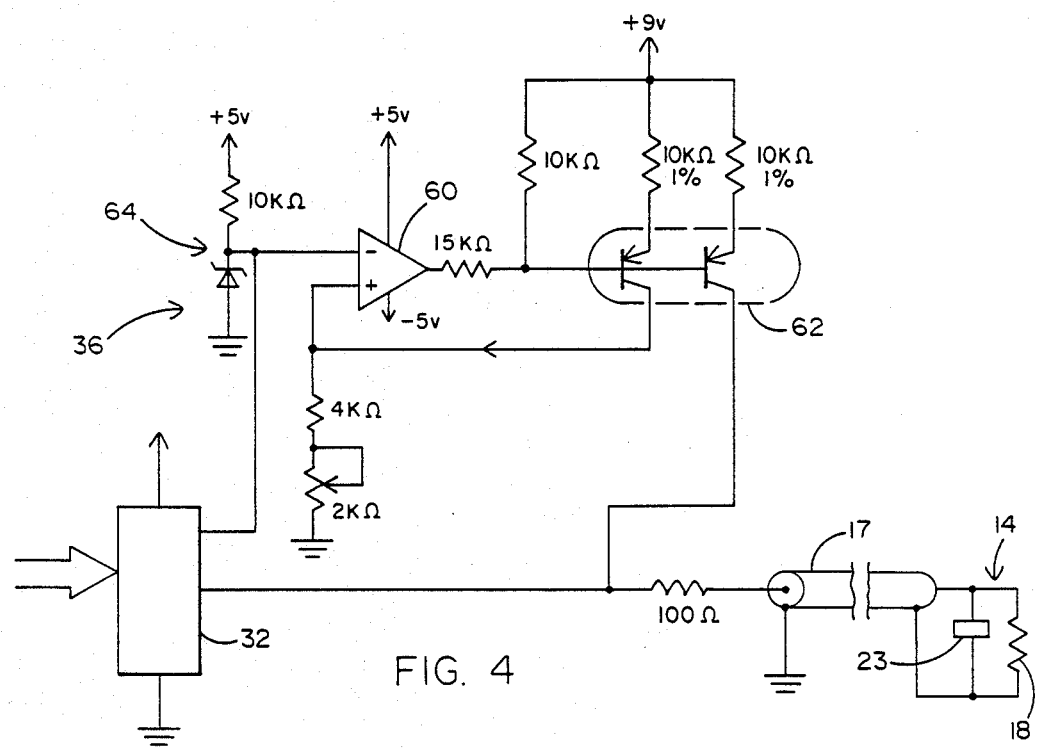
FIG. 4 is a schematic illustration of a preferred embodiment of the current source of the present invention.

The actual process of measuring resistor 18 in transducer 14 is accomplished by applying a fixed current of predetermined magnitude from current source 36 to the transducer 14 and across the code or tag resistor 18 and then measuring the voltage drop across the resistor which, of course, is determinitive of the resistance value thereof. Current source 36 is shown in more detail in FIG. 4. As shown in FIG. 4 current source 36 comprises an operational amplifier 60, a pair of matched transistors 62 and a zener diode circuit 64. The zener diode circuit provides a fixed reference voltage of approximately 1.2 volts. This reference voltage is applied to the negative input terminal of operational amplifier 60. The positive terminal of operational amplifier 60 is connected to a 4K Ohm fixed resistor in series with a 2K Ohm variable resistor and the voltage at the output of operational amplifier 60 is a function of the difference in voltage between its positive and negative input terminals. The output of operational amplifier 60 is applied through a 15K Ohm resistor to the common bases of the matched transistor pair 62, the emitters of which are connected to a nine volt source through 10K Ohm one percent resistors. The collector junctions of the transistor pair 62 provide two sources of current. One such source of current is applied to the resistor network a the positive input terminal of operational amplifier 60 thereby determining and the input to the positive terminal. The other such current is applied to the one-hundred Ohm damping resistor in series with coaxial cable 17 and transducer 14. Adjustment of the 2K Ohm variable resistor at the positive input terminal to operational amplifier 60 determines the error voltage or the difference voltage. Thus current source 36 provides a feedback circuit which permits precise control of the current derived from the matched transistor pair 62. In a preferred embodiment of the invention, the actual current derived from the circuit of FIG. 4 for use in recognizing the value of resistor 18 and transistor 14 is selected at 0.25 milliamps. It will also be seen in FIG. 4 that the A to D converter 32 is connected to the resistor 18 and transducer 14 through the coax cable 17 and the hundred Ohm damping resistor at the junction of the emitter of one of the transistors of matched pair 62. In this manner, the voltage applied to the A to D converter 32 for a fixed current of known magnitude determines the value of resistor 18 which may then be converted by converter 32 to a digital value.

The magnitude of the voltage drop across resistor 18 is provided as a digital signal to microprocessor 24 which uses that signal as an address in program memory 26 which contains a lookup table having a plurality of parameters for each indicated value of resistor 18. These parameters determine the automatic adjustments that must be made to optimize gauging circuit 20 for the transducer corresponding to the measured resistance of resistor 18. The parameter values determined by memory 26 and microprocessor 24 are applied to gauge control logic 22 which effectively loads various specific parameters controlling the operational characteristics of the gauge. By way of example, one such parameter is pulse repetition frequency for the pulse applied to the transducer. Another is the AGC (Automatic Gain Control) level of the receiver. Still another is pulse polarity and amplitude correction. Still another is selection of one of two available pulsers 50 and 52 depending upon whether the transducer is one selected for use with thin materials or one selected for use with thick attenuative materials. Switch 48, controlled by output latch 34 in response to the microprocessor 24, is used to control this parameter in response to the mode select characteristics of gauge control logic 22. System memory 26 is used to store the program which carries out the recognition adjustment and measurement operations of the gauge circuit 20 and switch 44 selects receiver sensitivity which is controlled by the output latch 34 and microprocessor 24 in response to the measured resistor value in transducer 14.

Figure 5:
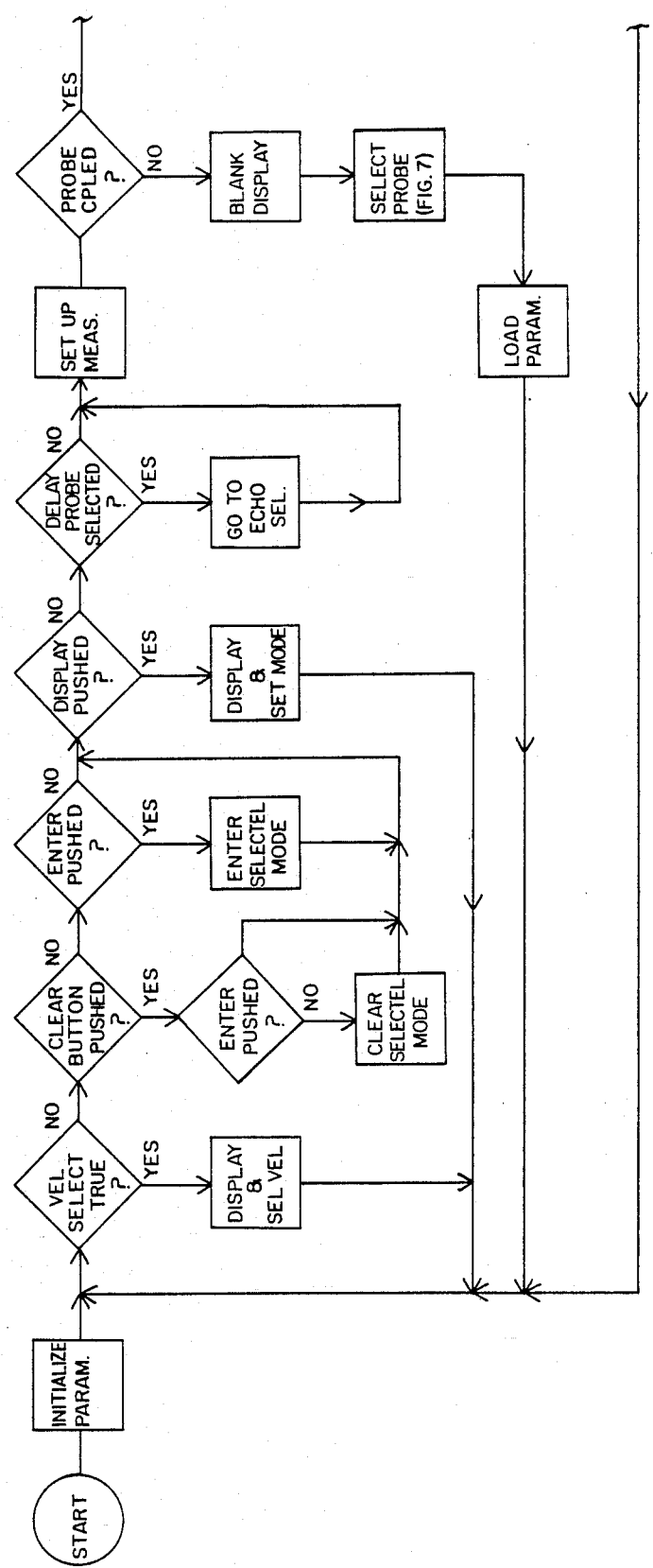
FIGS. 5, 6 and 7 together comprise a flow chart illustration of the program of the present invention.
Figure 6:
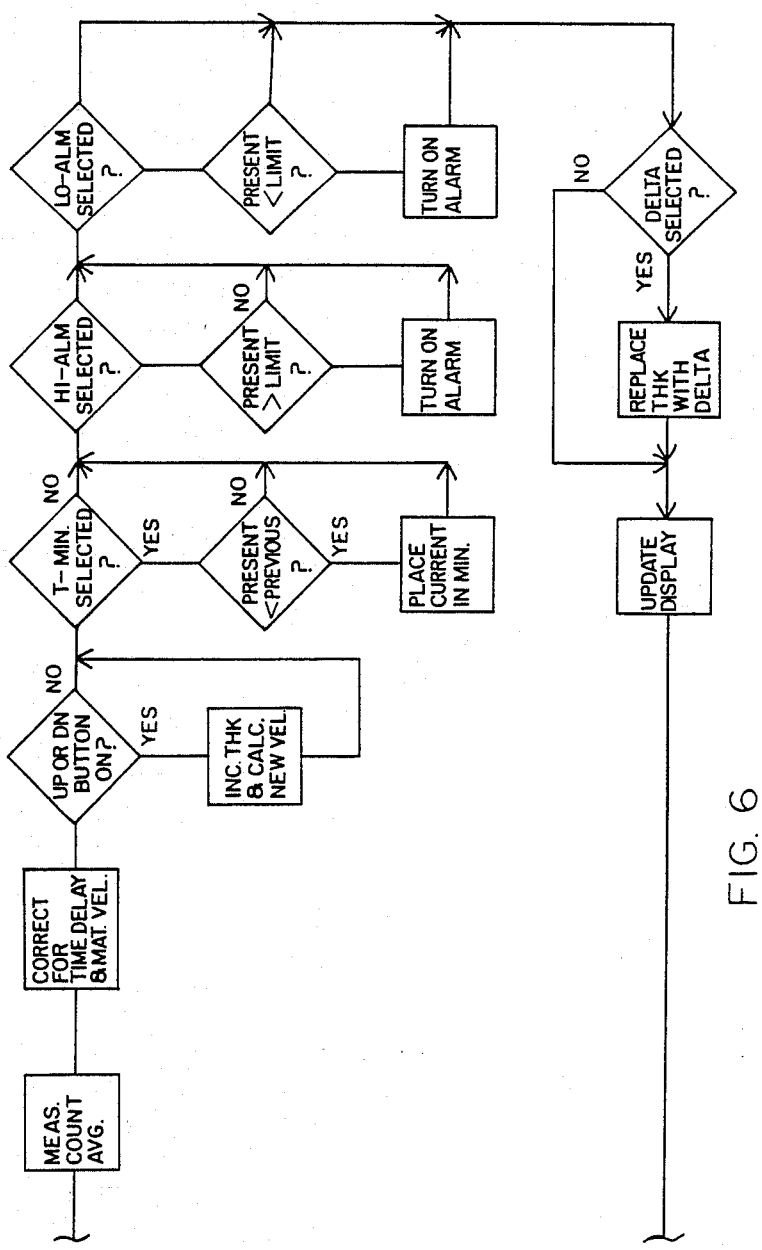
Figure 7:
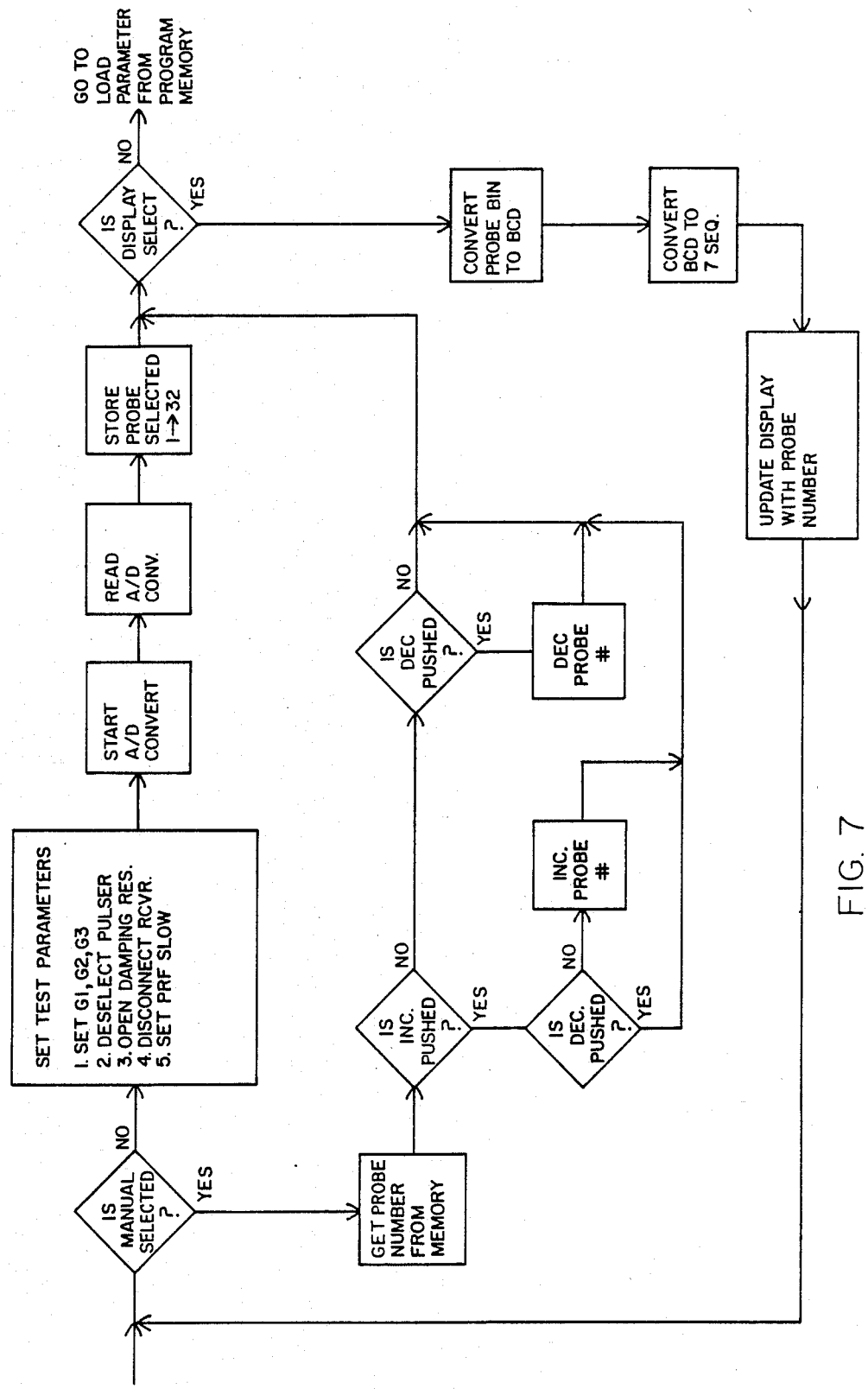

The actual operation of the gauge of the present invention may be best understood by reference to FIGS. 5, 6 and 7 which together constitute a flowchart of the program carried out in accordance with the method of the invention herein. Referring now to FIG. 5 through 7 it will be seen that the portion of the flowchart of the present invention illustrated in FIGS. 5 and 6 is substantially conventional in nature with the exception of those program operations which relate to selectional recognition of the probe or transducer and loading of the parameters to be used during the test in response to recognition of the probe. Thus, in FIG. 5 the first step in the program is to initialize parameters to a predetermined nominal value. The program then determines whether or not the velocity controls 13B of FIG. 1 have been depressed. If they have, the velocity is displayed and adjusted in accordance with the manual setting of the velocity controls. If the velocity controls have not been depressed, the program then checks whether certain other controls which may be provided in the present invention, such as a clear control, enter control and display control have been depressed. If they have, the program appropriately selects the operation responding to such controls and recycles. If none of these has been depressed, it then determines whether a delay probe has been selected and either sets an echo operation or not depending upon the status of this test.

The program then sets up the measurement of the thickness of the specimen in accordance with the depressed controls and checks to see whether the probe or transducer is coupled to the test specimen. If it is not, the display is blanked and the program goes on to select the probe number corresponding to the code or tag resistor within the transducer in accordance with the flowchart of FIG. 7 which will be discussed hereinafter. In other words, the program regards a decoupled transducer as one being tested for probe recognition. However, if the probe is coupled to the test specimen, the program carries out the operations shown in FIG. 6 wherein the first operation is to measure the average count between the transmitted and received pulse in order to measure the time delay therebetween. The actual measurement includes correction for time delay and material velocity. The program then checks whether the up or down velocity control has been depressed which would be normal operation during a calibration procedure to determine a material velocity for a material of known thickness. The program then checks whether minimum thickness and alarm settings have been selected which correspond to operation of the gauge shown in FIG. 1 but which do not encompass characteristics of the present invention per se. The program then checks whether Delta has been selected. Delta corresponds to a difference measurement instead of an absolute thickness measurement. If Delta has been selected, the measured thickness is replaced by the Delta measurement and if Delta has not been selected, the measured thickness is not replaced. In either case, the next step in the program is to update the display thereby presenting the measured thickness or Delta measurement to the user.

As previously indicated in conjunction with FIG. 5, there are two program steps shown in that figure which are unique to the present invention. These include the select probe step and the load parameter step. The select probe step involves program steps which are shown in more detail in FIG. 7. Referring now to FIG. 7 it will be seen that in carrying out the probe select function, the program of the present invention first determines whether or not the manual mode has been selected. This would occur if the user wishes to bypass the automatic transducer recognition function of the invention and in this case, the probe number would merely either stay the same or be increased or decreased in accordance with the user's manual control of a probe increment or decrement control switch. Accordingly, if the manual mode has been selected, the program obtains the probe number from memory which corresponds to the last probe number retained therein. The program then determines whether there has been an increment or decrement of the probe number set by the user and performs the requisite increment or decrement step accordingly. However, if the manual mode has not been selected, the program first sets the appropriate test parameters for probe recognition by setting the gates G1, G2 and G3 which are controlled by gauge control logic 22 of FIG. 3. It also deselects the pulser, opens the damping resistor circuit, disconnects the receiver and selects the slow pulse repetition frequency. In this manner, the gauge is now configured to conduct the probe recognition test by starting the A to D converter and then reading the A to D converter output which provides a digital readout of the voltage drop across the code or tag resistor 18 within the probe or transducer 14 as previously described. The corresponding probe number is then selected in accordance with the output of the A to D converter.

In the preferred embodiment of the invention disclosed herein, there are thirty-two (32) possible probe numbers that may be selected based upon the voltage drop across the resistor which, of course, is in turn dependent upon the value of the resistor 18. If the display select mode of operation of the gauge circuit 20 has been selected, the probe test is deemed to be merely a reporting mode which indicates through the display, what number probe or transducer is attached to the gauge circuit 20. Accordingly in this mode, the probe number is converted from binary to binary coded decimal and then subsequently to seven segment logic for output to the display which is updated with the probe number in the next step. The process is then repeated and ultimately if the display is not selected, parameters corresponding to the measured probe number are loaded from program memory 26 of FIG. 3 in the next step of the program, thereby providing all the appropriate circuit settings for the selected transducer.

Figure 8:
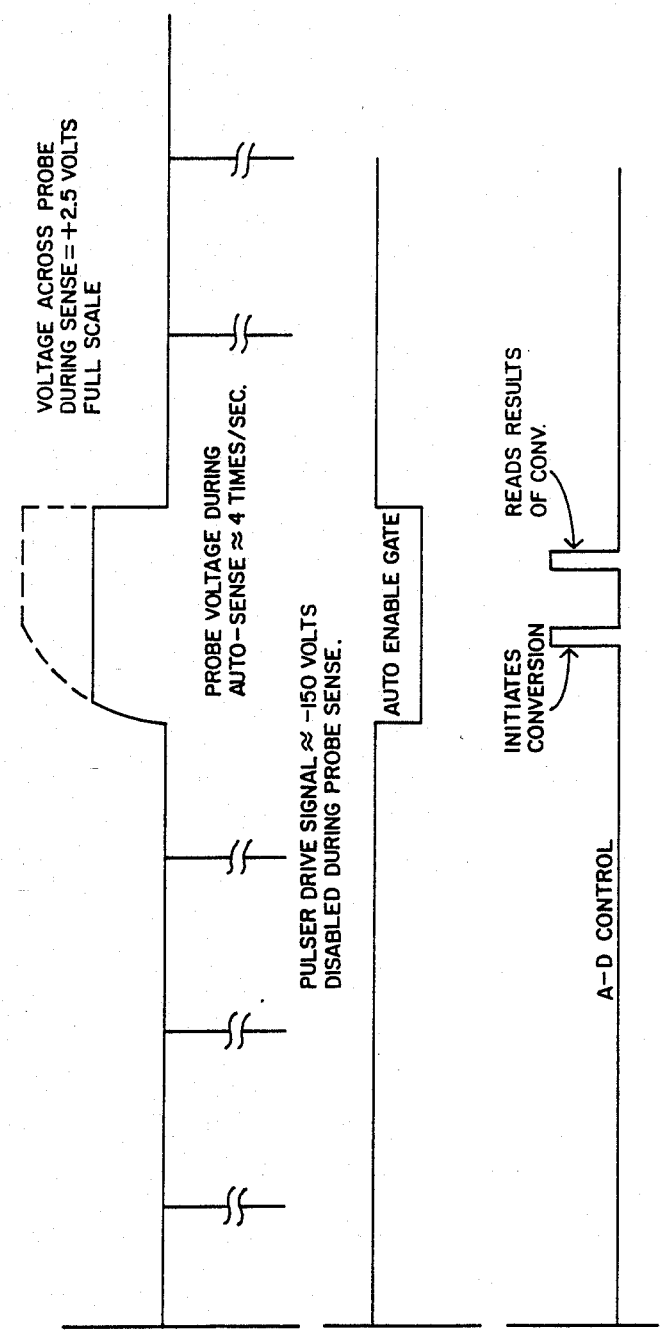
FIG. 8 is a timing diagram illustrating the operation of the present invention.

The timing between the application of the voltage across the probe and the initiation and results of the A to D converter process in shown in FIG. 8. As seen in FIG. 8, approximately four times per second, a voltage is applied to the probe resistor 18 at the same time an auto enable gate signal is applied to the A to D converter. This signal is one of the output signals of eight bit latch 34. Simultaneously, the pulser drive signal, which is approximately −150 volts, is disabled during the probe test to avoid any interference with the measurement of the tag or code resistor 18 in transducer 14.

It will now be understood that what has been disclosed herein comprises a measurement gauge which automatically recognizes each of a wide variety of transducers and then automatically and properly adjusts critical electronic parameters within the gauge to achieve optimum performance for the transducer and the application selected. A preferred embodiment of the invention uses an electrical component such as a resistor of unique value for each selected transducer type for permitting recognition of that transducer type when it is connected to the remaining portion of the gauge. The invention also comprises transducer recognition circuits which, in the preferred embodiment of the invention, comprise a microprocessor based digital implementation. The inventive concept disclosed herein can be readily applied to a variety of other instruments which use a variety of transducers such as industrial flaw detectors, bond testers, bolt gauges, ultrasound equipment, process control monitors, eddy current and microwave testers. The present invention also provides a method for optimizing a measurement gauge for the particular parameters of an external transducer to which it is connected. The steps comprise, placing in the transducer a device that uniquely identifies the type of transducer; recognizing the device and thus recognizing the type of the transducer; and setting gauge parameters in response to the recognized type of transducer.

Those having skill in the art to which the present invention pertains will, as a result of the applicants' teaching herein, now perceive various modifications and additions which may be made to the invention. By way of example, other circuit parameters, not specifically described herein, as well as other tagging and recognition schemes may be employed to implement the general concept of the present invention in a variety of different applications and more specifically, in virtually any measurement apparatus in which there is a replaceable transducer or other element, the selection of which makes it desireable to alter certain circuit parameters to optimize performance with each selected transducer or element. Accordingly, all such modifications and additions are deemed to be within the scope of the invention which is to be limited only by the claims appended hereto.

We claim:

1. In an ultrasonic thickness gauge of the type having a transducer to contact a workpiece, a pulser to transmit an ultrasonic pulse into the workpiece through the transducer, a receiver for receiving an echo of the transmitted pulse, a logic circuit for calculating the time elapsed between the transmitted and received pulses for measuring the thickness of the workpiece and a display for displaying measured thicknesses; the improvement comprising:

means in said transducer for identifying the type of transducer;
means in said gauge for automatically recognizing said transducer type identifying means;
means in said gauge, responsive to said recognizing means, for automatically setting gauge parameters in accordance with the recognized transducer type;
wherein said transducer type identifying means comprises an electrical component in the electrical circuit of said transducer;
wherein said recognizing means comprises a current source for applying electrical current to said component and means for measuring the voltage differential across said component induced by said current;
wherein said measuring means comprises an analog-to-digital converter;
wherein said setting means comprises a memory device having stored therein a plurality of parameter sets, each such set corresponding to an output of said analog-to-digital converter, said setting means further comprising means for controlling said gauge in accordance with said parameter sets; and
wherein at least one parameter in said parameter sets comprises the position of a decimal point in said display.

2. A method for use in an ultrasonic thickness gauge, the gauge of the type having a transducer to contact a workpiece, a pulser to transmit an ultrasonic pulse into the workpiece through the transducer, a receiver for receiving an echo of the transmitted pulse, a logic circuit for calculating the time elapsed between the transmitted and received pulses for measuring the thickness of the workpiece and a display for displaying the measured thickness; the method comprising the steps of:

(1) placing in said transducer a device for uniquely identifying the type of transducer;
(b 2) recognizing the device and thus recognizing the type of said transducer;
(3) setting gauge parameters in response to the recognized type of said transducer; and
wherein said device is an electrical component and wherein said placing step comprises the step of connecting said electrical component in parallel with the circuit of said transducer.

3. The method recited in claim 2 wherein said recognizing step comprises the step of measuring the electrical impedance of said electrical component.

* * * * *